United States Patent [19]

Cornell

[11] Patent Number: 5,032,178
[45] Date of Patent: Jul. 16, 1991

[54] DENTAL COMPOSITION SYSTEM AND METHOD FOR BLEACHING TEETH

[75] Inventor: John A. Cornell, West Chester, Pa.

[73] Assignee: Demetron Research Corporation, Danbury, Conn.

[21] Appl. No.: 473,822

[22] Filed: Feb. 2, 1990

[51] Int. Cl.$^5$ .......................... A61K 7/20; C11D 3/395
[52] U.S. Cl. ............................. 106/35; 252/186.41; 424/7.1; 424/49; 424/53; 433/215; 433/216
[58] Field of Search .......................... 424/7.1, 49, 53; 106/35; 433/215, 216; 252/186.41

[56] References Cited

U.S. PATENT DOCUMENTS

| | | | |
|---|---|---|---|
| 1,717,723 | 6/1929 | McCall | 424/7.1 |
| 3,243,377 | 3/1966 | Stolar | 252/95 |
| 4,223,003 | 9/1980 | Scheller | 424/49 |
| 4,528,180 | 7/1985 | Schaeffer | 424/53 |
| 4,537,765 | 8/1985 | Gaffar et al. | 424/53 |
| 4,655,953 | 4/1987 | Oakes | 252/99 |
| 4,661,070 | 4/1987 | Friedman | 433/215 |
| 4,696,757 | 9/1987 | Blank et al. | 252/186.29 |
| 4,731,196 | 3/1988 | Staten et al. | 252/184 |
| 4,788,052 | 11/1988 | Ng | 424/53 |
| 4,822,375 | 4/1989 | Lang et al. | 8/423 |
| 4,876,082 | 10/1989 | Romeo | 424/7.1 |
| 4,895,721 | 1/1990 | Drucker | 424/53 |
| 4,983,381 | 1/1991 | Zaragoza | 424/53 |

FOREIGN PATENT DOCUMENTS 58-180420 10/1983 Japan ...................... 424/53

*Primary Examiner*—Paul Lieberman
*Assistant Examiner*—Linda D. Skaling
*Attorney, Agent, or Firm*—E. Lieberstein

[57] ABSTRACT

A dental composition and method for bleaching vital and non-vital teeth, comprising a preselected, concentrated, aqueous solution of hydrogen peroxide and a nonaqueous component mixed to form an aqueous gel or paste, with the nonaqueous component including an inert silica gelling agent, an accelerator, a plasticizer and thickening agent, and means for establishing a substantially fixed time period for treating the teeth in response to the application of optical energy. A redox color indicator is used to transform from one color to another over the fixed time period to provide a visual indication that the treatment is completed, as well as an indication that the peroxide solution was active.

6 Claims, No Drawings

DENTAL COMPOSITION SYSTEM AND METHOD FOR BLEACHING TEETH

FIELD OF THE INVENTION

This invention relates to a dental composition and method for bleaching vital and non-vital teeth.

BACKGROUND OF THE INVENTION

One commonly noticed problem during the normal development of the human dentition, particularly in adults, is the discoloration of the teeth. Discoloration in adult teeth is primarily characterized by a gradual yellowing of the teeth, which is presently attributed to the normal aging process. Teeth may also be discolored or blemished by staining. Stains are classified in two separate categories defined as extrinsic or intrinsic. An intrinsic stain may be attributed to ferric-containing salts, which are absorbed into the body in geographical areas containing high concentrations of iron in the water supply, or from tetracycline stains, which occur, for example, in utero during the third trimester of pregnancy. Examples of extrinsic stains are diet-related, such as from tea and/or coffee, or habit-related, such as from tobacco chewing and cigarette smoking.

One method for treating discoloration in teeth is bleaching. Dentists have used bleaching to treat discoloration in vital and non-vital teeth. Because of the very different physiology of these teeth, dentists have developed two different methods of treatment, using a common bleaching solution. Presently, non-vital bleaching consists of placement of a rubber dam for isolating the tooth, preparing an opening in the pulp chamber into which a concentrated bleaching solution of about thirty-three percent (33%) hydrogen peroxide is placed, with a similar solution placed on the surface of the tooth. During this process, the tooth is heated externally by use of a heating instrument similar in design to an electric soldering iron or by means of a heat lamp to raise the temperature at the treated tooth to a range of about 120° F. to 160° F. The procedure takes approximately forty-five minutes. Vital bleaching uses the same concentrated hydrogen peroxide bleaching solution, but is placed only on the external lingual and labial surfaces of the teeth and heated for about forty-five minutes, in the same manner as described for non-vital bleaching. The present bleaching method causes great patient discomfort and potentially can cause gingival trauma. There is also substantial danger from the use of the electric heating element, which can cause burns and injury to adjacent teeth. The bleaching solution can easily run up or down the surface of the tooth and find its way into the gingival crevice, causing a severe burn of the gingiva, which is painful and difficult to heal. Moreover, there is no way for the dentist to know if the concentrated hydrogen peroxide solution is active or to what extent it has deteriorated, since its shelf life is very limited, with the hydrogen peroxide readily dissociating into water and oxygen.

OBJECTS OF THE INVENTION

It is an object of the present invention to provide a gel or paste of concentrated hydrogen peroxide as an oral composition for bleaching teeth. Another object of the present invention is to provide a gel or paste of concentrated hydrogen peroxide and a viscosity controlling ingredient which permits the paste or gel to be built up on the tooth surface without sagging under the influence of gravity. It is another object of the present invention to provide an aqueous hydrogen peroxide gel or paste which contains a redox color indicator which provides the operator with a visual indication of the activity rate of the hydrogen peroxide in the gel or paste.

It is an even further object of the present invention to apply an aqueous peroxide gel or paste to a stained tooth surface which will cause the hydrogen peroxide to penetrate the tooth surface to reach the stained area, with patient treatment initiated in accordance with the present invention by application of optical energy within the light energy spectrum of between 400 and 700 nanometers.

SUMMARY OF THE INVENTION

The dental bleaching composition of the present invention overcomes all of the shortcomings of the prior art use of a concentrated hydrogen peroxide solution. The dental composition of the present invention is preferably packaged as a two-component system, with one of the components represented by a conventional concentrated solution of hydrogen peroxide, and with the other component comprised of an aggregate mixture of dry constituents which, when combined in an appropriate proportion with the concentrated aqueous hydrogen peroxide component, forms a gel or paste, with hydrogen peroxide remaining the principal bleaching constituent. The paste or gel may readily be applied to a specified tooth or surface area of the tooth where bleaching is desired. Furthermore, the dental composition does not require a heat source, and bleaching occurs over a short, controlled period of time, generally under fifteen minutes. The entire treatment time period is controlled by optically initiating the bleaching operation with a light source, and terminating the operation upon visual color transformation of the paste or gel from a firs to a second color, such as from green to colorless.

The dental composition of the present invention includes a nonaqueous component adapted to be mixed with a concentrated aqueous solution of hydrogen peroxide to form an aqueous paste or gel for direct in-situ application to the teeth to be bleach, with said first component comprising in combination:

an inert silica gelling agent;

a catalytic accelerator;

an agent for providing thixoplasticity and thickening properties to the composition, such as celluose ethers and methyl vinyl ethers; and means for indicating completion of the bleaching treatment of the teeth, comprising a redox color indicator for transforming from one color to another in response to the dissociation of hydrogen peroxide over a given time period.

DETAILED DESCRIPTION OF THE INVENTION

The aforementioned ingredients of the nonaqueous component of the dental bleaching composition of the present invention is critical to the performance of the present invention. Hydrogen peroxide is available to dentists in a thirty to thirty-five percent (30%–35%) aqueous solution. The nonaqueous component of the composition of the present invention permits the dentist to prepare an active bleaching composition in a solid form, either as a paste or gel, for direct application to the teeth to be bleached, with the period of treatment initiated photo-optically for activating the composition and terminated by removal of the paste or gel from the treated teeth upon a visual color transformation after a fixed time period. The color transformation will occur only if hydrogen peroxide dissociates to a concentration of nascent oxygen sufficient to cause color transformation of the color indicator in the composition within that time frame The color indicator is, accordingly, for practical purposes, a critical component which must be compatible with the other components and yet provide a distinct, uniform color to the gel or paste composition, which will oxidize and transform to another color or become colorless in response to the level of activity, corresponding to the dissociation of concentrated hydrogen peroxide over a fixed time period. Only guinea green and, to a lesser extent, phenolphthalin, has been found to satisfy this requirement of the invention. The concentration of guinea green in the gel or paste has little effect on its color transformation characteristic. It is thus a direct indicator of hydrogen peroxide activity. If the hydrogen peroxide used in forming the gel or paste was of a low concentration due to aging, no significant color change will occur in the time frame set for treating the patient, independent of the concentration of the color indicator in the gel.

Guinea green is a commercially available dye sold by the Aldrich Chemical Company, having the chemical identity: ethyl [4-(p-[ethyl (m-sulfobenzyl) amino]-alpha-phenylbenzylidene-2,5-cyclohexadien-1-ylidene) (m-sulfobenzyl) ammonium hydroxide inner salt sodium salt. Guinea green colors the composite material green and provides an identity of the activity level of the material by becoming colorless when sufficiently oxidized. If the hydrogen peroxide component has deteriorated due to age, insufficient oxidation will occur to neutralize the green color. It is at present difficult for a practicing dentist to know if the hydrogen peroxide supply in the dental office is active, since its activity is dependent upon storage time and temperature. It is also important to permit the hydrogen peroxide to penetrate the enamel in order to lighten the enamel of he teeth. The guinea green will neutralize to provide the total absence of color over a total treatment time period of from about five (5) to fifteen (15) minutes for the composition of the present invention.

Phenolphthalin is a colorless crystal derived from phenolphthalein which converts to a reddish color when sufficiently oxidized. This is a less preferred redox indicator. The concentration level of the color indicator is not a critical factor and, in fact, only a minor percent, of between 0.01 and 0.3 percent by volume, is all that is necessary to produce an intense color.

The preferred ratio of the aqueous hydrogen peroxide component to the nonaqueous component is 50 to 100 parts by volume, with a more preferred ratio of 50 to 70 parts by volume, with 60 parts being optimum. Stated otherwise, the preferred ratio is five parts of the nonaqueous powder to three parts hydrogen peroxide.

The inert silica gelling agent in the nonaqueous component is preferably an amorphous fumed silica. Fumed silica are silicon dioxide particles of extremely small size, substantially below one (1) micron. The preferred concentration of the silica gelling agent in the nonaqueous component is between fifty to eighty percent (50%–80%) by volume, and is the major ingredient of this component, as well as of the gel or paste.

Another essential ingredient of the nonaqueous component is the incorporation of an accelerator for controlling the breakdown of hydrogen time period. The preferred accelerator is manganese sulfate monohydrate. "Oxone," a potassium persulphinate product of the du Pont Corporation may also be used in combination, in instance the Oxone functions as a co-catalyst. The range for use of each component of the accelerator is indicated in the Table of examples.

The dissociation of hydrogen peroxide is initiated, in accordance with the invention, by the use of a dental curing light. The optical energy accelerates the catalyst for activating and promoting the acceleration of free radical polymerization of hydrogen peroxide, and by use of a redox color indicator, as discussed heretofore, for timing the duration of the bleaching operation after it is initiated. Preferably light energy in the visible spectrum of between 400 and 700 nanometers should be used to initiate the breakdown of hydrogen peroxide. The application of light energy may be maintained for the entire treatment period, but preferably at least about three minutes. The color indicator, as explained heretofore serves as a critical component for providing a visual indication of the completion of treatment, and as an indicator that the hydrogen peroxide was, in fact, active during treatment.

As an alternative to manganese sulfate, ferrous sulfate may be used as the catalytic activator and at essentially the same concentration level. In fact, using ferrous sulfate, it is possible to activate the composition at room temperature without the application of visible light. However, in such case a quiescent period of at least about five to seven minutes is necessary before catalytic activity begins to become meaningful. Thus, the ability to control the initiation of the operation is lost and much more time is necessary to complete treatment. Accordingly, it is preferred to operate with the application of light energy which provides a more effective control over catalytic activity. Manganese sulfate is preferred when applying light and has been found to be responsive to light energy, thereby accelerating catalytic activity during the application of light energy to provide a complete treatment in under ten to fifteen minutes.

The remainder of the nonaqueous formulation is provided by a polymethylvinyl ether maleate potassium salt polymeric compound or cellulosics, preferably selected from the class consisting of carboxymethyl cellulose, hydroxyethyl cellulose and sodium cellulose sulfate. The preferred compound is sold under the trademark name Gantrez (MS-955) by the GAF Corporation of New Jersey. The polymethylvinyl ether maleate potassium salt or celulosic ether compound is also essential to the nonaqueous formulation, and provides thermoplasticity and thickening properties to the paste or gel composition formed with hydrogen peroxide, so as to permit the paste to be built up upon the teeth to be bleached and remain essentially erect, i.e., the material does not sag or slump during the treatment period. It also slows drying of the composition to maintain the level of activity on the tooth surface throughout the treatment time period. It is important that the gel or paste remain aqueous for the entire treating period and yet remain physically stationary and in place on the tooth surface to permit maximum surface interaction and prevent gingival damage. It is postulated that the hydrogen peroxide must penetrate the enamel of the tooth while dissociating to maximize bleaching. The combination of the silica gelling agent and the cellulose ether compound represents the major constituents of the nonaqueous formulation, and preferably should equal at least about eighty percent (80%) of such composition.

The following table indicates the preferred range for each constituent in the nonaqueous component and illustrates eight (8) examples of varying concentrations for the constituents, with example number (1) being the preferred composition. In the other seven examples, one element is eliminated or modified, with the other constituents adjusted relative to example number (1) functioning as the control for comparison purposes:

TABLE

| | Constituent | Range (Percent) |
|---|---|---|
| (a) | Silica absorbent gelling agent | 50-75 |
| (b) | (1) Manganese sulfate monohydrate | 2-10 |
| | (2) Oxone | 0-10 |
| | (3) Ferrous sulfate | 2-10 |
| (c) | Gantrez | remainder to 25 |
| (d) | Guinea green | 0.01-0.3 |

EXAMPLES

| Constituent | EXAMPLES | | | | | | | | |
|---|---|---|---|---|---|---|---|---|---|
| | (1) | (2) | (3) | (4) | (5) | (6) | (7) | (8) | (9) |
| (a) | 70 | 70 | 70 | 70 | 30 | 100 | 70 | 70 | 70 |
| (b-1) | 4.8 | 1.8 | 4.8 | 0 | 4.8 | 4.8 | 4.8 | 4.8 | — |
| (b-2) | 5.75 | 0 | 5.75 | 5.75 | 5.75 | 5.75 | 5.75 | 15.0 | — |
| (b-3) | — | — | — | — | — | — | — | — | 4 |
| (c) | 19.24 | 19.24 | 0 | 19.24 | 19.24 | 19.24 | 30 | 19.24 | 19.24 |
| (d) | 0.1 | 0.1 | 0.1 | 0.1 | 0.1 | 0.1 | 0.1 | 0.1 | 0.1 |

The formulation of example one (1) was the easiest to mix and apply. The composition did not dry out during bleaching. The process required three (3) to five (5) minutes of light activation and a total of about ten (10) minutes until the color changed from green to white. The formulation was applied to a stained tooth with the stain appreciably reduced upon completion of the process. Examples three (3), six (6), and seven (7) were failures in that the material dried too quickly and did not appear to bleach as well. Example five (5) did not form a satisfactory paste or gel and, accordingly, was too difficult to apply. Examples two (2) and four (4) provided results similar to example one (1), but took almost twice the time, indicating insufficient accelerator. Example eight (8) appeared unstable during storage, indicating the presence of an excess of Oxone. Example nine (9) used no light and at room temperature (23° C.) began bubbling in six (6) minutes and turned light brown (from green) after nine minutes.

I claim:

1. A dental composition for bleaching vital and nonvital teeth, comprising a concentrated aqueous solution of hydrogen peroxide having above at least about thirty percent (30%) by volume hydrogen peroxide and a nonaqueous component suspended in said concentrated hydrogen peroxide solution in a ratio of 50 to 100 parts by volume hydrogen peroxide solution to 100 parts by volume of said nonaqueous component for direct in vivo application to the teeth to be bleached, with said nonaqueous component comprising:
   fifty to eighty percent (50% to 80%) by volume or inorganic particles of silica;
   two to ten percent (2% to 10%) by volume of a catalytic activator selected form the class consisting of manganese sulfate monohydrate and ferrous sulfate;
   0.01% to 0.5% by volume of a redox color indicator selected from the class consisting of ethyl[4-{p-[ethyl (m-sulfobenzyl)amino]-alpha-phenylbenzylidene{-2,5-cyclohexadien-1-ylidene](m-sulfobenzyl) ammonium hydroxide inner salt sodium salt and phenolphthalin; and
   the remainder composed of a plasticizing and thickening agent selected from the class consisting of polymethylvinyl ether maleate potassium slat, carboxymethyl cellulose, hydroxyethyl celluose and sodium cellulose sulfate.

2. A dental composition, as defined in claim 1, wherein said silica is an hydrated, amorphous silica in a concentration of form fifty to seventy-five percent (50% to 75%) by volume of the nonaqueous component.

3. A dental composition, as defined in claim 2, wherein said thickening agent is a polymethylvinyl ether maleate potassium salt.

4. A method for bleaching teeth in vivo comprising formulating an aqueous bleaching gel or paste for immediate application by mixing a concentrated aqueous solution of hydrogen peroxide of above at least thirty percent (30%) by volume hydrogen peroxide and a nonaqueous component in a ratio of 50 to 100 parts by volume hydrogen peroxide solution to 100 parts by volume of said nonaqueous component, with said nonaqueous component comprising: inert fifty to eighty percent (50% to 80%) by volume of particles of silica; two to ten percent (2% to 10%) by volume of a catalytic activator selected from the class consisting of manganese sulfate monohydrate and ferrous sulfate; and the remainder composed of a thickening agent selected from the class consisting of cellulose ethers and methyl vinyl ethers; applying said aqueous gel or paste to the teeth to be bleached, and initiating the bleaching treatment process by applying to the tooth surface to be treated optical energy within the light spectrum of 400 to 700 nanometers.

5. A process as defined in claim 4, further comprising the step of adding a redox color indicator to said nonaqueous component, selected from the class consisting of ethyl [4-{p-[ethyl (m-sulfobenzyl)amino]-alpha-phenylbenzylidene{-2,5-cyclohexadien-1-ylidene](m-sulfobenzyl) ammonium hydroxide inner salt sodium salt and phenolphthalin.

6. A process, as defined in claim 5, wherein said particles of silica and said plasticizing and thickening agent constitute over eighty percent (80%) by volume of the nonaqueous component.

* * * * *